United States Patent [19]
Maier

[11] Patent Number: 5,533,993
[45] Date of Patent: Jul. 9, 1996

[54] MEDICATION INJECTOR WITH PROTECTED CANNULA AND Y-SITE LOCKOUT

[75] Inventor: Gunther L. Maier, Yorba Linda, Calif.

[73] Assignee: International Medication Systems, Limited, South El Monte, Calif.

[21] Appl. No.: 543,150

[22] Filed: Oct. 13, 1995

Related U.S. Application Data

[63] Continuation of Ser. No. 317,689, Oct. 5, 1994, abandoned.

[51] Int. Cl.[6] .................................................. A61B 19/00
[52] U.S. Cl. ........................ 604/411; 604/403; 604/905
[58] Field of Search .................................. 604/82, 83, 86, 604/87, 88, 89, 90, 91, 92, 200, 201, 412, 413, 415, 416, 411, 905, 403; 141/329, 383

[56] References Cited

U.S. PATENT DOCUMENTS

| | | |
|---|---|---|
| Re. 33,617 | 6/1991 | Ogle, II . |
| D. 267,199 | 12/1982 | Koenig . |
| 3,378,008 | 4/1968 | Ogle . |
| 3,739,780 | 6/1973 | Ogle . |
| 3,923,059 | 12/1975 | Ogle . |
| 3,942,514 | 3/1976 | Ogle . |
| 3,976,073 | 8/1976 | Quick et al. . |
| 4,203,443 | 5/1980 | Genese ................................ 604/413 |
| 4,232,669 | 11/1980 | Nitshke . |
| 4,295,476 | 10/1981 | Quaas .................................. 604/415 |
| 4,296,747 | 10/1981 | Ogle . |
| 4,467,588 | 8/1984 | Carveth . |
| 4,516,967 | 5/1985 | Kopfer . |
| 4,607,671 | 8/1986 | Aalto et al. ........................... 141/383 |
| 4,737,144 | 4/1988 | Choksi . |
| 4,752,292 | 6/1988 | Lopez et al. . |
| 4,759,756 | 7/1988 | Forman et al. . |
| 4,869,384 | 9/1989 | Ogle, II . |
| 5,069,225 | 12/1991 | Okamura ............................. 604/412 |
| 5,086,780 | 2/1992 | Schmitt ............................... 604/403 |
| 5,344,417 | 9/1994 | Wadsworth, Jr. .................... 604/411 |
| 5,356,380 | 10/1994 | Hockwater et al. ................. 604/905 |

FOREIGN PATENT DOCUMENTS

WO92/11897  7/1992  WIPO .

*Primary Examiner*—Corrine M. Maglione
*Assistant Examiner*—N. Kent Gring
*Attorney, Agent, or Firm*—Christie, Parker & Hale

[57] ABSTRACT

A medication injector for use with an inlet port having an imperforate closure for a conduit connected to and extending away from a container for liquid intended for intravenous administration includes a boss which carries a cannula with a scarf at one end spaced from the boss. The cannula scarf is adapted to puncture the inlet port closure. An elongated and generally cylindrical sheath is secured to the boss and extends around the cannula and extends beyond the scarf end of the cannula. An outwardly extending annular flange on the sheath prevents the cannula from being inserted into an injection port of a Y-site of an intravenous administration set, yet permits the cannula to be inserted into the inlet port of the i.v. container.

15 Claims, 5 Drawing Sheets fig. 1 fig. 2

MEDICATION INJECTOR WITH PROTECTED CANNULA AND Y-SITE LOCKOUT

CROSS REFERENCE TO RELATED APPLICATION

This is a continuation of application Ser. No. 08/317,689, filed Oct. 5, 1994, now abandoned.

BACKGROUND OF THE INVENTION

This invention relates to injectors for administering medication with a syringe and a hypodermic needle or cannula.

Many different types of syringes and hypodermic needles have been used for administering various types of medications. U.S. Pat. No. 3,378,008 to Ogle (1968) discloses a hypodermic syringe and vial prefilled with an injectable liquid, such as medication to be administered to a patient. Although that type of syringe has been successful, it has the disadvantage of presenting an exposed needle, which can cause an accidental injury, infection, or exposure to dangerous and toxic medication.

U.S. Pat. No. Re 33,617 to Ogle, II (1991) discloses injection apparatus which includes a protective sheath disposed around the sharp end of a hypodermic needle to prevent accidental sticking. This device has been widely accepted by the industry. However, it does not have any kind of a lockout feature to prevent medication from being administered inadvertently through an improper site, which might subject a patient to medication at a rate in too high a concentration for the safety of the patient. For example, some medication, such as morphine sulfate, is sold as a fairly concentrated medication, e.g., 50 mg of morphine sulfate per milliliter of solution, and must therefore be diluted, say, in an intravenous bag or container of saline solution, or mounted in a pump which limits delivery of the medication to safe increments over a safe period of time.

Because of the dangerous nature of certain drugs or medications, they have been sold in packages of relatively low volume to minimize the possibility of overdosing. However, this is inconvenient because it requires a large number of individual containers and adds to the work of medical personnel in administering the medication to patients.

SUMMARY OF THE INVENTION

This invention provides a medication injector with a hypodermic needle surrounded by a protective sheath to prevent accidental sticking. Moreover, a lockout device on the sheath prevents the injector from being used to administer medication in the syringe in a concentrated form to a patient.

Briefly, this invention provides a medication injector for use with an inlet port having an imperforate elastomeric closure for a conduit connected to and extended away from a container for liquid intended for intravenous (i.v.) administration. Many such containers have at least two conduits, one through which medication can be injected into the solution in the container, and the other for delivering liquid in the container to an infusion catheter inserted in the vein of a patient. The latter conduit often has a "Y-site" which carries a short lateral tube to provide an injection site through which additional or supplemental medication can be supplied directly to the vein of a patient. Although many types of medication can be safely applied through the injection port of a Y-site, some drugs, such as a concentrated solution of morphine sulfate, cannot. It is, therefore, important that such medication be administered through a procedure which prevents inadvertent overdosing. The injector of this invention prevents inadvertent overdosing. The injector includes a boss which carries a cannula or hypodermic needle with a scarf at one end spaced from the boss. The cannula scarf is adapted to puncture the imperforate closure of an inlet port of an i.v. container. An elongated and generally cylindrical sheath is secured at one end to the boss, and extends away from the boss to surround the cannula and extend beyond the scarf end of the cannula at a first open end of the sheath. The internal diameter of the first open end of the sheath is sufficiently small to protect the user from inadvertent puncture of the hands or fingers by the scarf. An outwardly extending annular flange on the sheath, at and around the first open end, is constructed and arranged to engage a tubular portion adjacent an injection port of a Y-site of an intravenous administration set and thereby prevent the scarf end of the cannula from puncturing the injection port of the Y-site. The end of the sheath secured to the boss is adapted to make a fluidtight seal with a source of medication to be introduced through the cannula to the inlet port of the container.

The internal diameter of the first open end of the sheath is sufficiently large to permit the sheath to slip over the conduit which carries the imperforate closure to form the inlet port for the container of liquid intended for intravenous administration. The outside diameter of the flange around the open end of the sheath is sufficiently small to not interfere with the insertion of the cannula through the imperforate closure for the inlet port of the container. Preferably, the flange outside diameter is greater than about 20 millimeters to insure proper interference to prevent inadvertent connection of the injector to an injection port of a Y-site. Preferably, the flange diameter is less than about 40 millimeters to avoid interference with adjacent conduits when the injector is to be connected to the inlet port of IV container. Preferably, the ratio of the outside diameter of the flange to the inside diameter of the sheath is between about 2 to 1 and about 4 to 1.

In the preferred form of the invention, the injector includes a guide with a second fitting shaped to make a releasable fluidtight seal with the fitting connected to the sheath portion. The second fitting has a passageway extending through it to be connected with the passageway extending through the fitting connected to the sheath. An elongated second cannula has one end connected to the passageway of the second fitting. The other end of the second cannula is adapted to be connected to the source of liquid medication with means for causing the liquid medication to flow into the i.v. container and mix with liquid stored in it. Preferably, a tubular guide is secured to the second fitting to extend around the second cannula. The guide is constructed and arranged to receive a syringe barrel which holds the liquid medication so a resilient stopper disposed at an open end of the barrel to confine the liquid in the barrel can be penetrated by the second cannula so that thereafter sliding the stopper relative to the barrel causes the liquid in the barrel to flow into the container and mix with the other liquid stored in that container.

In the presently preferred form of the invention, one of the fittings has a tapered socket, and the other has a tapered nozzle, and the two fittings are adapted to be held together by a threaded connection.

Preferably, the inside diameter of the protective sheath around its open end is less than about 16 mm to provide against accidental puncture or injury with the scarf end of the cannula surrounded by the sheath. The inside diameter sheath is less than the length of that part of the cannula surrounded by the sheath to provide a geometry which prevents accidental sticking of the user with the scarf end of the cannula surrounded by the sheath, and the length of the cannula projecting from the boss is sufficient to penetrate the closure of the inlet port of the i.v. container when the injector sheath is slipped over the inlet port.

DESCRIPTION OF THE PREFERRED EMBODIMENTS

Referring to the drawings, an injector 10 includes an elongated, hollow, cylindrical protective sheath 12 open at a receiving (left as viewed in FIGS. 2 and 3) end 13. Preferably, all components of the injector, except the cannulas, are made of a suitable moldable plastic, such as a polycarbonate, which is of radiation grade to permit sterilization by conventional irradiation. A bore 14 extends through the sheath from the receiving end to a transfer end 15, which is integrally formed with an inwardly extending, transverse, annular wall 16 (FIGS. 2 and 3), which has a central bore 18 around which is formed integrally with wall 16 a collar 17 which makes a snug fit around a hollow, cylindrical boss 20 coaxially disposed in the transfer end of the sheath. For the embodiment of FIG. 3, the collar and boss may be sealed together with an adhesive (not shown), or by spin-welding.

A relatively small diameter bore 22 in the boss adjacent end wall 16 steps up to a larger diameter bore 24, which tapers outwardly to the right (as viewed in FIG. 3) to form a first fitting in the shape of a Luer-Lock female socket 30 connector. The Luer-Lock may be of the type shown in U.S. Pat. No. 4,737,144 to Choksi (1988).

A first or short cannula 32 is sealed at its right (as viewed in FIGS. 2 and 3) end in the small bore 22 of the Luer-Lock female fitting. The left end of the first cannula includes a scarf or tapered section to present a sharp point 36 extending toward the receiving (left) end of the injector. The scarf 36 is adapted to penetrate a resilient, imperforate closure 38 covering a conduit 39 to form an inlet port 40 of a container 42, such as an i.v. bag, which holds an i.v. solution 43.

An outwardly extending annular flange 44 is formed integrally with the receiving end 13 of the protective sheath. The outside diameter of the flange is sufficiently large to contact a delivery conduit 45 (FIG. 1) and thus prevent the injector sheath from being slipped far enough over an injection port 46 of a Y-site 47 to cause the cannula scarf to pierce a closure 48 for the port. However, the outside diameter of the flange is not so large as to contact an outlet conduit 49 of the i.v. bag and prevent the injector sheath from being slipped onto the injection port so the cannula can properly penetrate the closure 38 for the inlet port to permit medication to be injected into the bag as shown on the left side of FIG. 1, and described in more detail below.

Figure 2:
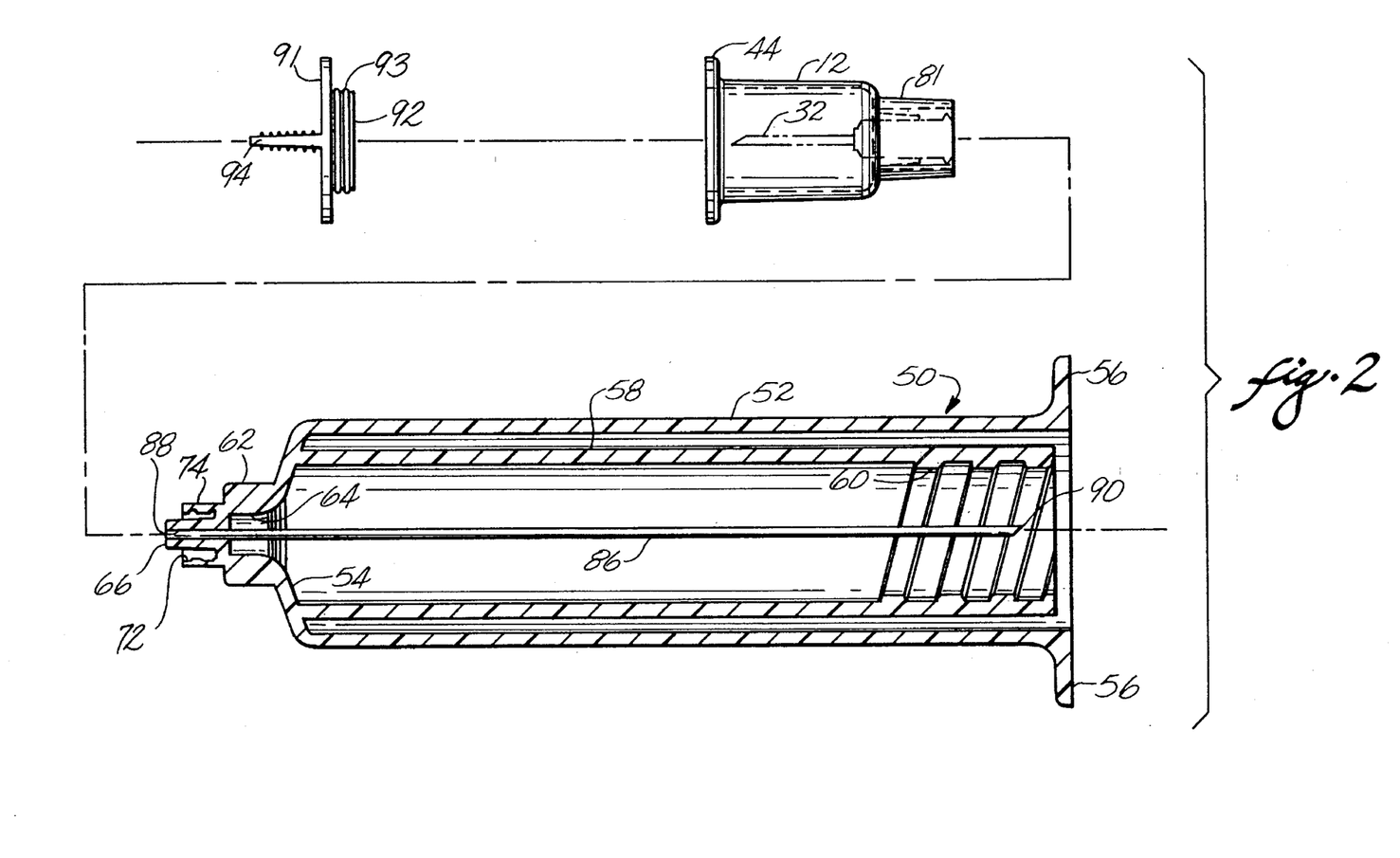
FIG. 2 is an enlarged exploded view, partly in cross section, of the protective sheath disconnected from the guide.
Figure 3:
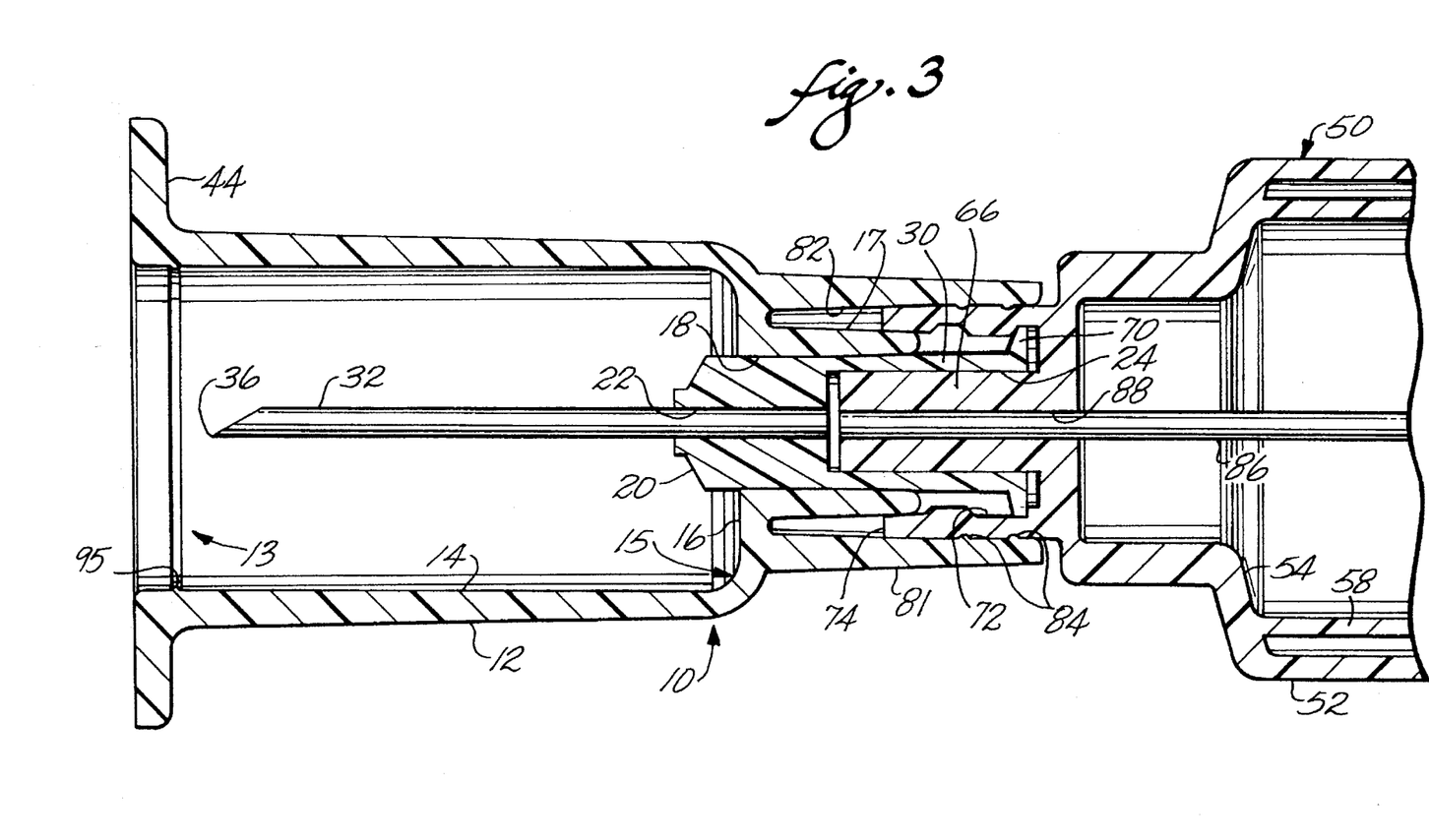
FIG. 3 is an enlarged fragmentary sectional view showing the protective sheath connected to the guide.

A tubular injector guide 50 includes an elongated cylindrical outer sleeve 52 formed integrally at a discharge end (left as viewed in FIGS. 2 and 3) with the outer periphery of an annular discharge end wall 54, which slopes inwardly to the left (as viewed in FIGS. 2 and 3).

A pair of diametrically opposed and outwardly extending ears 56 (FIG. 1) are formed integrally with the inlet end (right as viewed in FIGS. 2 and 3) of the injector outer sleeve 52 to lie in a plane perpendicular to the longitudinal axis of the injector and guide. A cylindrical inner sleeve 58 spaced from and disposed coaxially within the outer sleeve is formed integrally at its discharge end (left) with the interior surface of annular wall 54. The inlet end (right) of the inner sleeve is substantially co-extensive with the inlet end of the outer sleeve and has internal threads 60, as described below.

The discharge end of the injector includes an external annular boss 62 formed integrally with the exterior of the annular wall 54 around a central bore 64 extending through the end wall and boss.

A second fitting in the shape of an externally tapered Luer-Lock nozzle 66 connector is formed integrally on the left (as viewed in FIGS. 2 and 3) end of the boss 62, and makes a snug fit in a matching tapered socket 30 of the Luer-Lock female first fitting. External threads 70 around the right (as viewed in FIG. 3) end of the Luer-Lock socket 30 engage internal threads 72 in a cylindrical skirt 74 formed integrally with the boss 62 and disposed to surround part of the Luer-Lock nozzle. When the threads on the two fittings are screwed together, they releasably lock and seal the nozzle in the socket, as shown in FIG. 3.

An external annular shield 81 is formed integrally with the exterior of the annular wall 16 at the right (as viewed in FIG. 3) end of the injector. The shield 81 surrounds and is spaced from collar 17. The interior surface 82 of the shield tapers outwardly toward the right and makes a snug fit around a matching external surface of the skirt 74, which surrounds the nozzle of the Luer-Lock. Optionally, if an even tighter fit is desired, a pair of inwardly extending and longitudinally spaced annular protrusions 84, which are semicircular in the cross-sectional view shown in FIG. 3, bear against the external surface of the skirt 74 to provide a tight seal against contamination when the Luer-Lock fitting is in the connected position shown in FIG. 3. However, these protrusions are optional, and a sufficient seal can be attained without them.

A second or long cannula 86, disposed coaxially within the injector guide 50, is sealed at its left (as viewed in FIGS. 2 and 3) in a central bore 88 extending through the nozzle and collinear with the central bore 22 in the boss in the end wall 16 of the injector. The right end of the second cannula includes a scarf 90 (FIG. 2), which terminates just short of the right end of the inner sleeve 58.

Figure 1:
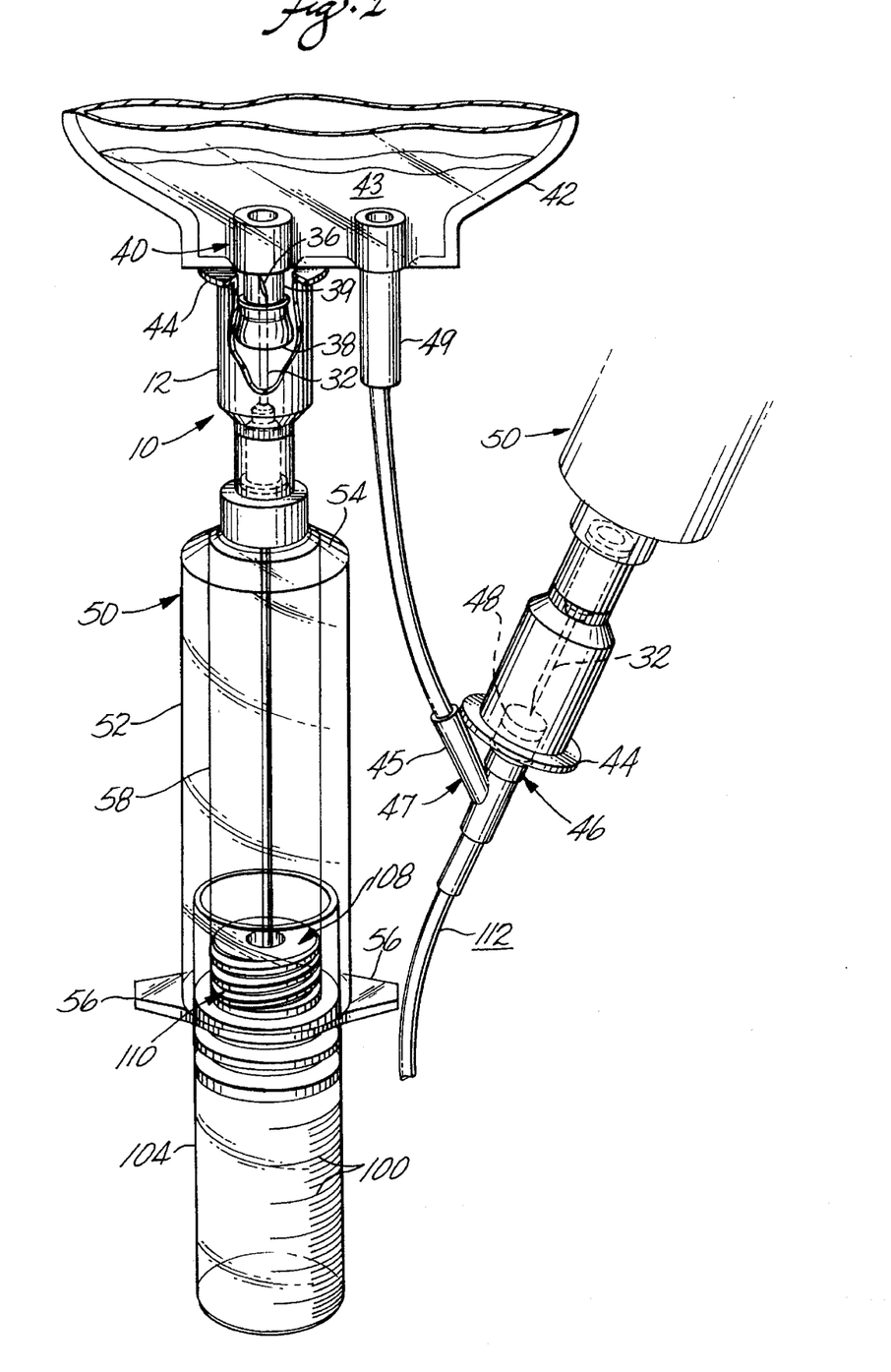
FIG. 1 is a perspective view, partly broken away, showing an injector of this invention properly connected to the inlet port of an intravenous container, and also showing how the flange on the sheath prevents connecting the injector to an injection port of a Y-site.

When the injector and injector guide are assembled, as shown in FIG. 3, the cannulas and the Luer-Lock fittings form a passageway through which a liquid (not shown) can pass to mix with i.v. solution in the i.v. bag, when the injector is slipped over the inlet port of the i.v. bag, as shown on the left side of FIG. 1.

Referring to FIG. 2, an injector cap 91 having a centrally located cylindrical and inwardly extending plug 92 with external grooves 93 can be snapped into the left (as viewed in FIGS. 2 and 3) end of the protective sheath and thus seal it against contamination. An outwardly extending handle 94 in the shape of a web is formed integrally across the diameter of the cap 91 to facilitate installing and removing the cap from the protective sheath. An inwardly extending annular projection 95, which is semicircular in cross section as viewed in FIG. 3, around the interior of the left end of the protective sheath engages the grooves 93 of cap 91 to act as a detent and thus releasably secure the cap in the protective sheath. A similar cap (not shown) is adapted to be fitted into the right (as viewed in FIGS. 2 and 3) end of the injector guide to seal it against contamination.

Figure 4:
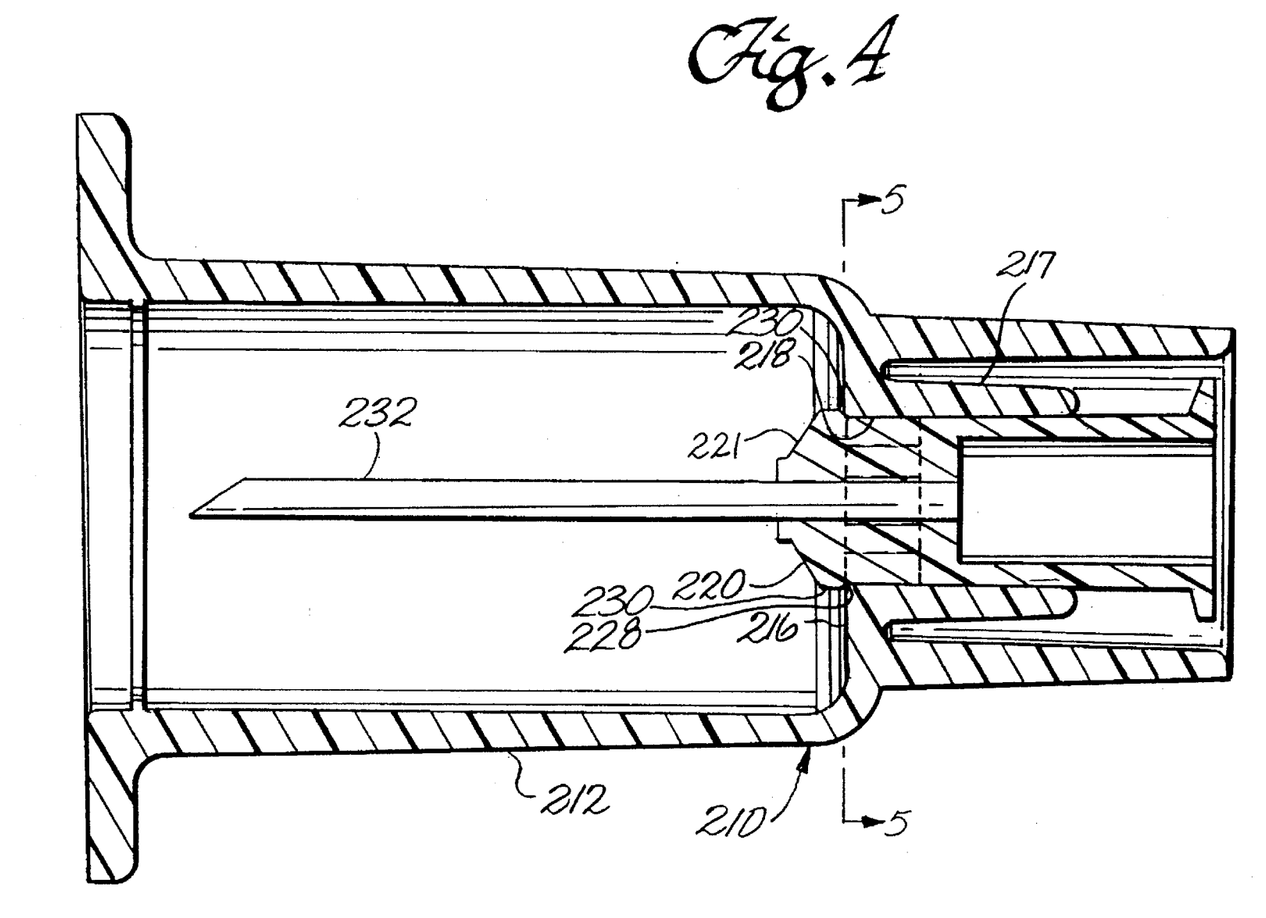
FIG. 4 is an enlarged fragmentary sectional view showing another embodiment of a protective sheath connected to a guide.
Figure 5:
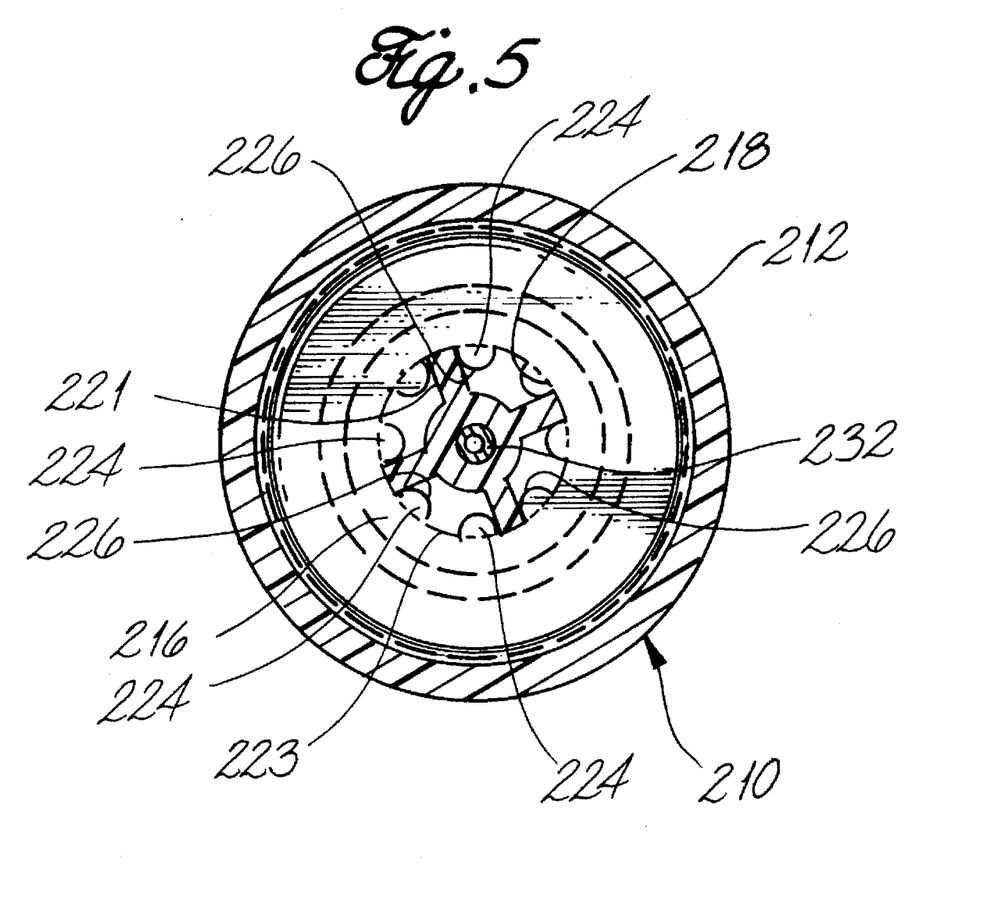
FIG. 5 is a sectional view of the protective sheath and guide of FIG. 4 taken along line 5—5.

In another preferred embodiment, as shown in FIGS. 4 and 5, an injector 210 includes a sheath 212 in which a collar 217 for the sheath is joined by a friction fit to a boss 220, which holds the cannula 232. As shown in FIG. 5, the boss has four radially and longitudinally extending fins 221 spaced equidistant around the cannula 232. The collar includes eight inwardly opening, longitudinal slots 223 spaced equidistant around its central bore 218. Each slot lies between adjacent inwardly and longitudinally extending ridges 224, which are semicircular in cross section (as viewed in FIG. 5) to present inwardly facing convex surfaces 226 to facilitate fitting the boss in the collar. In assembling the injector, the boss is pressed into the collar so that the four fins mesh with four of the eight slots of the collar. By including eight slots with the adjacent convex surfaces, the slots are symmetrically disposed relative to the fins so assembly is simplified because the orientation of the parts to one another is not critical.

In the embodiment of FIGS. 4 and 5, a tight fit between the collar and boss is promoted by proper selection of materials of construction. Preferably, the sheath, including the collar, is made of a material such as polycarbonate while the boss is made of a softer material such as polypropylene. Preferably, the fins extend out slightly further than the inner diameter of the collar, as measured from the bottom of one groove to the bottom of a diametrically opposed groove. Thus, the bottoms of the grooves lie in a cylindrical plane which has a diameter slightly less than that of a cylindrical plane defined by the outermost portions of the fins. Upon insertion of the boss into the collar, the softer fins deform plastically to create a tight friction fit with the collar. The travel of the boss into the collar is limited by the right (as viewed in FIG. 4) ends of the ridges 224 on the collar abutting the left end of the boss. The fit of the boss and collar is further improved by including a sharp edge 228 at the juncture of the annular wall 216 and the bore 218 of the collar 217 so the softer and deformed fins cold-flow outwardly as they pass the sharp edge so the inner end of each fin forms a respective hook 230 over the sharp edge to lock the boss firmly to the collar. This is best illustrated in FIG. 4.

With the injector and injector guide assembled as shown in FIG. 3 or FIG. 4, and the protective caps in their respective positions, the assembled apparatus is packaged and sterilized (say, by conventional irradiation) until ready for use as shown in the operating position of FIG. 1.

To use the injector/injector guide assembly, it is removed from the sterile container, and the cap (not shown) is removed from the right (as viewed in FIGS. 2 and 3) end of the injector guide 50. A cylindrical syringe barrel 104, which may be of conventional construction such as that shown in U.S. Pat. No. 3,378,008, includes the usual calibration marks 106 indicating the amount of liquid medication (not shown) in the barrel. A slidable stopper 108 is disposed in the outlet end (upper end as viewed in FIG. 1) of the barrel to store the liquid in the barrel under sterile conditions until ready for use. The stopper includes a reduced-diameter portion 110, which is externally threaded, and which extends toward the upper end of the syringe barrel. A syringe cap (not shown) usually makes a snug fit within the outlet of the syringe barrel and fits over the reduced portion 110 of the stopper. In this condition, the cap, stopper, syringe barrel, and the liquid within are sterilized in a sealed package (not shown) until ready for use, as explained below.

To use the apparatus of this invention, the cap is removed from the calibrated syringe barrel. The stoppered end of the syringe barrel is then inserted into the annular space between the inner and outer sleeves of the injector guide until the external threads on the reduced portion 110 of the stopper 108 in the syringe barrel first engage the internal threads 60 in the inner sleeve of the injector. This contact is made gently, and then, without pushing, the syringe barrel is rotated about three turns to engage the threads until a slight resistance is felt. An additional half turn of the syringe barrel causes the scarf end of the long cannula to pass through the syringe barrel stopper so that the liquid medication within the barrel is now in communication through the two cannulas with the liquid in the i.v. bag.

With the syringe barrel assembled as described, the injector protective sheath is slipped up over the inlet port to the position shown in FIG. 1 so that the scarf end of the short cannula 32 penetrates the closure 38 to provide communication with the interior of the i.v. bag. To this end, and as shown in FIGS. 3 and 4, the distance from the scarf end of the cannula to the open end of the sheath is less than that of the internal diameter of the sheath around the scarf end of the cannula. As previously stated, the outside diameter of the flange 44 is sufficiently small so as not to contact the adjacent outlet conduit 49. Thus, the injector can be properly positioned over the inlet port 40, as shown in FIG. 1. Conversely, as shown on the right side of FIG. 1, the outside diameter of the flange 44 is sufficiently large to prevent the protective sheath from being slipped far enough onto the injection port 46 of the Y-site 47 to permit cannula 32 to penetrate the closure 48 of the injection port.

With the apparatus assembled as shown in FIG. 1, the syringe barrel is then pushed into the injector guide, using the ears 56 on the injector to facilitate operation with one hand, if desired. The stopper is held in a fixed position in the threaded end of the inner sleeve of the injector guide so that the closed end of the syringe barrel slides toward the stopper and forces liquid out of the barrel, through the cannulas, and into the container 42, where it mixes with the i.v. solution there. After the required amount of medication is injected into the i.v. bag, the injector is moved away from the i.v. bag, causing the short cannula to be withdrawn from the inlet port.

Thus, with the apparatus assembled as shown in FIG. 1, the medication in the syringe barrel 104 can be injected only into the inlet port of the i.v. bag, where the medication is safely mixed and diluted with i.v. solution before being administered to a patient (not shown) through the outlet conduit 49, Y-site 47, and a delivery tube 112, which is connected to a catheter (not shown) inserted in a vein of the patient.

If the medication in the syringe barrel is to be administered in some manner other than that shown in FIG. 1, say, by a pump, or directly into an injection port, or into a vein of a patient, the injector can be removed from the injector guide by simply unscrewing the Luer-Lock connection.

Thereafter, the male nozzle of the Luer-Lock can be connected to a "needleless" connection, and the injector guide and syringe barrel mounted in a pump (not shown), which is driven in a controlled manner to deliver medication at the required rate. If desired, the nozzle end of the Luer-Lock fitting can be connected to a conventional hypodermic needle for administration of the medication.

I claim:

1. A medication injector for use with an inlet port having an imperforate closure for a conduit connected to and extending away from a container for liquid intended for intravenous administration, the injector including a boss carrying a cannula with a scarf at one end spaced from the boss, the cannula scarf being adapted to puncture the imperforate closure of the inlet port, an elongated and generally cylindrical sheath having a first open end surrounding the cannula and extending beyond the scarf end of the cannula at the first open end of the sheath, the distance from the scarf end of the cannula to the open end of the sheath being less than that of the internal diameter of the sheath around the scarf end of the cannula, the sheath being affixed to the boss, the internal diameter of the first open end of the sheath being less than about 16 millimeters to protect the user from inadvertent puncture of the hands and fingers by the scarf; and an outwardly extending annular flange on the sheath at and around the said open end, the flange being constructed and arranged to have an outside diameter of at least 20 millimeters so as to engage a tubular portion adjacent an injection port of a Y-site of an intravenous administration set and thereby prevent the scarf end of the cannula from puncturing the injection port of the Y-site, the boss having a bore extending through it in communication with the cannula, and the boss having a fitting in the shape of a Luer-Lock connector disposed around the bore and being adapted to make a releasable fluidtight seal with a mating Luer-Lock connector connected to a source of medication to be introduced through the cannula to the inlet port of the container.

2. Apparatus for intravenously administering to a patient a liquid medication which must be administered only in relatively small increments over a relatively long period of time, or diluted with a liquid in a container through an inlet port having an imperforate closure in a conduit connected to and extending away from the container, the apparatus including a boss carrying a first cannula with a scarf at one end spaced from the boss, the first cannula scarf being adapted to puncture the imperforate closure of the inlet port, an elongated and generally cylindrical sheath having a first open end surrounding the first cannula and extending beyond the scarf end of the first cannula at the first open end of the sheath, the distance from the scarf end of the cannula to the open end of the sheath being less than that of the internal diameter of the sheath around the scarf end of the cannula, the sheath being affixed to the boss, and having an internal diameter less than about 16 millimeters whereby the user is protected by said cylindrical portion from inadvertent puncture of the hands and fingers by the scarf; an outwardly extending annular flange on the sheath at and around the said open end, the flange being constructed and arranged to have an outside diameter of at least 20 millimeters so as to engage a tubular portion adjacent an injection port of a Y-site of an intravenous administration set and thereby prevent the scarf end of the first cannula from puncturing the injection port of the Y-site, the boss having a bore extending through it in communication with the cannula;

a first fitting in the shape of a Luer-Lock connector having a passageway extending through it, the first fitting being secured to the boss so the passageway through the first fitting is connected to the first cannula;

a second fitting in the shape of a Luer-Lock connector adapted to make a releasable fluidtight seal with the Luer-Lock connector on the first fitting and having a passageway extending through it to be connected with the first fitting; and an elongated second cannula having one end connected to the passageway of the second fitting, the other end of the second cannula being adapted to be connected to a source of a liquid with means for causing the liquid to flow into the container and mix with the liquid in it.

3. Apparatus for intravenously administering to a patient a liquid medication which must be administered only in relatively small increments over a relatively long period of time, or diluted with a liquid in a container through an inlet port having an imperforate closure for a conduit connected to and extending away from the container, the apparatus including a boss carrying a first cannula with a scarf at one end spaced from the boss, the first cannula scarf being adapted to puncture the imperforate closure of the inlet port, an elongated and generally cylindrical sheath having a first open end surrounding the first cannula and extending beyond the scarf end of the first cannula at the first open end of the sheath, the distance from the scarf end of the cannula to the open end of the sheath being less than that of the internal diameter of the sheath around the scarf end of the cannula, the sheath being affixed to the boss, and having an internal diameter less than about 16 millimeters whereby the user is protected by said cylindrical portion from inadvertent puncture of the hands and fingers by the scarf; an outwardly extending annular flange on the sheath at and around the said open end, the flange being constructed and arranged to have an outside diameter of at least 20 millimeters so as to engage a tubular portion adjacent an injection port of a Y-site of an intravenous administration set and thereby prevent the scarf end of the first cannula from puncturing the injection port of the Y-site, the boss having a bore extending through it in communication with the cannula;

a first fitting in the shape of a Luer-Lock connector having a passageway extending through it, the first fitting being secured to the boss so the passageway through the first fitting is connected to the first cannula;

a second fitting in the shape of a Luer-Lock connector adapted to make a releasable fluidtight seal with the Luer-Lock connector on the first fitting and having a passageway extending through it to be connected with the first fitting passageway;

an elongated second cannula having one end connected to the passageway of the second fitting, the other end of the second cannula being adapted to be connected to a source of a liquid with means for causing the liquid to flow into the container and mix with the liquid in it; and a tubular guide secured to the second fitting and around the second cannula, the guide being constructed and arranged to receive a syringe barrel holding the liquid medication so a resilient stopper disposed in an open end of the barrel to confine the liquid in the barrel can be penetrated by the said other end of the second cannula so that after the said penetration by the second cannula, sliding the stopper relative to the barrel will cause the liquid in the barrel to flow into the container and mix with the liquid in it.

4. Apparatus according to claim 2 or 3 in which one fitting has a tapered socket, and the other fitting has a tapered nozzle.

5. Apparatus according to claim 2 or 3 in which one fitting has a tapered socket, the other fitting has a tapered nozzle, and the two fittings are adapted to be held together by a threaded connection.

6. Apparatus according to claim 1, 2, or 3 in which the sheath inside diameter is between about 10 and about 16 millimeters.

7. Apparatus according to claim 1, 2, or 3 in which the outside diameter of the flange is between about 20 and about 40 millimeters.

8. Apparatus according to claim 1, 2, or 3 in which the ratio of the outside diameter of the flange to the inside diameter of the sheath is between about 2:1 and about 4:1.

9. Apparatus according to claim 1, 2, or 3 in which the inside diameter of the sheath is less than the length of the cannula from the boss to the scarf.

10. A medication injector including a boss carrying a cannula with a scarf at one end spaced from the boss, an elongated and generally cylindrical sheath having a first open end surrounding the cannula and extending beyond the scarf end of the cannula at the first open end of the sheath, and an annular collar secured to the sheath and friction-fitted to the boss, the boss having a bore extending through it in communication with the cannula, and the boss being adapted to make a fluidtight seal with a source of medication to be introduced through the cannula to the inlet port of the container, the collar being made of one plastic and the boss being made of a different and deformable plastic which is softer than that of the collar, the boss and collar being pressed together with sufficient force to cause the boss to deform and flow with respect to the collar.

11. An injector according to claim 10 in which the annular collar includes longitudinally extending and inwardly opening grooves, and the boss includes longitudinally and outwardly extending fins which each make a snug friction fit in a respective groove.

12. An injector according to claim 11 in which there are more grooves than fins.

13. An injector according to claim 12 in which the grooves are symmetrically disposed relative to the fins.

14. An injector according to claim 11, 12, or 13 in which the fins are dimensioned relative to the grooves so that the fins deform as they are pressed into the grooves.

15. An injector according to claim 14 in which the fins are deformed and forced to cold-flow around the collar to lock the boss and collar together.

* * * * *